June 9, 1964
C. ANDERSON
Plant Pat. 2,410
PLUM TREE
Filed March 15, 1963
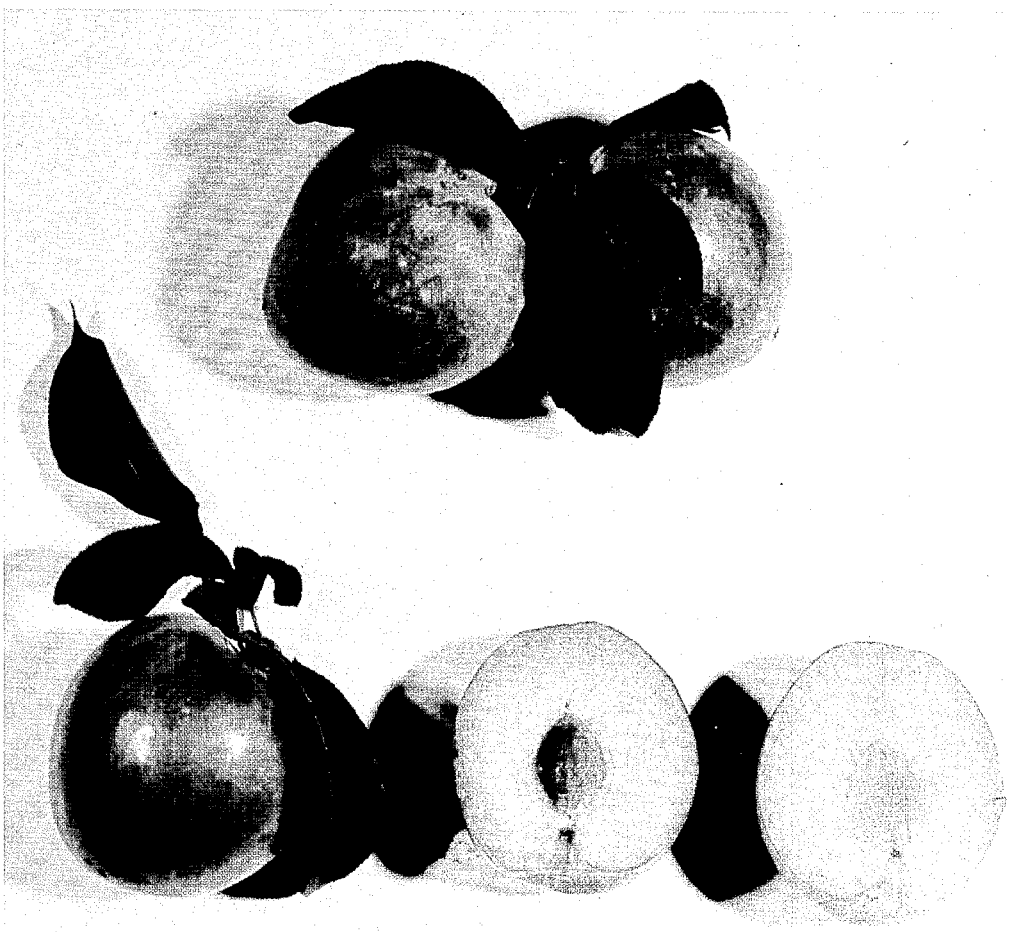
INVENTOR
*Cleve Anderson*
BY *Webster & Webster*
ATTYS.

United States Patent Office

Plant Pat. 2,410
Patented June 9, 1964

2,410
PLUM TREE

Cleve Anderson, 429 N. Maple St., Manteca, Calif.

Filed Mar. 15, 1963, Ser. No. 265,568
1 Claim. (Cl. Plt.—38)

This discovery relates to a new and distinct variety of plum tree which is very productive and a regular bearer of relatively small, semi-freestone fruit having firm golden flesh and a green skin.

The present variety of plum tree is particularly characterized, as to novelty, by a relatively late harvest which spans a period of a month or longer without the fruit becoming overripe on the tree; by remaining firm in shipment, or in cold storage for a substantial length of time, although picked eating ripe when sweet and edible; by good eating quality and delicious flavor; and by the flesh of the fruit being firm, crisp and meaty.

In comparison with existing and well-known varieties of plum trees, the fruit of the present variety resembles the Kelsey in general skin color but with a faint red blush on the sunny side adjacent the blossom end, and with a near-white bloom; is in harvest about five weeks later than the Kelsey; is shaped quite similar to the Santa Rosa but is slightly more plump; and has a flavor similar to the Burbank Standard but is somewhat sweeter, and with less acid than the Santa Rosa.

The herein claimed variety of plum tree was discovered by me, growing as a chance seedling, on my ranch located near Kingsburg, county of Fresno, State of California. After discovery of the original tree, and the recognition by me of the distinctive nature of its fruit, I asexually reproduced the variety by grafting it on mature orchard trees at my ranch located as aforesaid; such reproductions in maturity having run true to the parent in all respects.

The drawing comprises an illustration, by photographic reproduction in color, of the fruit and leaves; one fruit being cut in half to expose and show the flesh, and with the stone remaining in place in one of such halves.

Referring now more specifically to the pomological details of this new and distinct variety of plum tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Medium.
- *Growth.*—Upright.
- *Density.*—Dense.
- *Form.*—Vase-shaped.
- *Hardiness.*—Hardy.
- *Production.*—Very productive.
- *Bearing.*—Compatible with Santa Rosa and Wickson but will set fruit without cross-pollination. Regular bearer.

Trunk:
- *Form.*—Stocky.
- *Texture.*—Medium.

Branches:
- *Form.*—Medium.
- *Texture.*—Medium.
- *Color.*—Brown, dull.
- *Lenticels.*—Numerous; small.

Leaves:
- *Size.*—Medium. Average length—3" to 3½". Average width—1" to 1½".
- *Form.*—Lanceolate; acutely pointed.
- *Thickness.*—Medium.
- *Color.*—Top side—medium to dark green (22–L–7). Under side—lighter green (21–E–6).
- *Texture.*—Smooth.
- *Margin.*—Crenulate.
- *Petiole.*—Medium length; thick.
- *Glands.*—Average number—two. Opposite; small; reniform; green; positioned at base of leaf adjacent petiole.

Flower Buds:
- *Hardiness.*—Hardy.
- *Size.*—Small.
- *Length.*—Medium.
- *Form.*—Pointed; appressed.

Flowers:
- *Blooming period.*—Date of first bloom—March 13, 1962. Date of full bloom—March 21, 1962. Medium as compared to other varieties as, for example, the Santa Rosa.
- *Size.*—Medium.
- *Color.*—White.

Fruit:
- *Maturity when described.*—Eating ripe—September 14, 1962.
- *Date of first picking.*—September 4th.
- *Date of last picking.*—October 4th.
- *Size.*—Uniform; small. Average diameter axially—2". Average transversely in suture plane—2".
- *Form.*—Tends to be heart-shaped; symmetrical.
- *Suture.*—Relatively inconspicuous; shallow.
- *Ventral surface.*—Rounded very slightly.
- *Cavity.*—Rounded. Average depth—¼". Average breadth—¼".
- *Base.*—Rounded.
- *Apex.*—Rounded to truncate.

Skin:
- *Thickness.*—Medium.
- *Texture.*—Medium.
- *Tenacity.*—Tenacious to flesh.
- *Tendency to crack.*—Slight.
- *Color.*—Green plus yellow (21–L–6) with a faint red blush (5–K–10) on sunny side adjacent blossom end. Near-white bloom.
- *Down.*—Moderate.

Flesh:
- *Color.*—Golden (11–L–7).
- *Amygdalin.*—Wanting.
- *Juice.*—Moderate.
- *Texture.*—Firm; crisp; meaty.
- *Fibers.*—Few.
- *Ripens.*—Evenly.
- *Flavor.*—Sweet; subacid.
- *Aroma.*—Distinct but relatively slight.
- *Eating quality.*—Fair to good.

Stone:
- *Type.*—Semifree; adheres to flesh at points on both upper sides; free over most of stone area.
- *Size.*—Small. Average length—⅞". Average breadth—⅝". Average thickess—¼".
- *Sides.*—Equal; flattened.
- *Surface.*—Regularly furrowed near ventral edge.
- *Ridges.*—Jagged; continuous.

*Pits.*—Elongated.
*Ventral edge.*—Thin.
*Dorsal edge.*—Narrow, without groove.
*Color.*—Brown (15–E–11).
*Tendency to split.*—Slight.

Use: Market; dessert; culinary; canning.
Keeping Quality: Good.
Shipping Quality: Good.

All of the herein identified previously known and existing varieties of plum trees are unpatented.

The tree and its fruit herein described may vary in slight detail due to climatic and soil conditions under which the variety may be grown; the present description being of the variety as grown in the Central Valley of California.

The following is claimed:

A new and distinct variety of plum tree substantially as illustrated and described, which is very productive and a regular bearer of semi-freestone fruit having golden flesh and a green skin with a faint red blush adjacent the blossom end; such fruit being characterized by a relatively late harvest spanning at least a month without the fruit on the tree becoming overripe, but remaining firm in shipment or cold storage although picked when eating ripe, and by firm, crisp and meaty flesh; and further characterized by a resemblance to the Kelsey in general skin color but in harvest about five weeks later, by a shape similar to the Santa Rosa but slightly more plump, and by a flavor similar to the Burbank Standard but sweeter, and with less acid than said Santa Rosa.

No references cited.